(12) United States Patent
DiFranco

(10) Patent No.: US 6,835,324 B1
(45) Date of Patent: Dec. 28, 2004

(54) METHOD FOR ISOLATING OLEIC ACID AND PRODUCING LINELOIC DIMER/TRIMER ACIDS VIA SELECTIVE REACTIVITY

(75) Inventor: Elso DiFranco, Callaway, FL (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

(21) Appl. No.: 09/512,228

(22) Filed: Feb. 24, 2000

Related U.S. Application Data
(60) Provisional application No. 60/121,529, filed on Feb. 25, 1999.

(51) Int. Cl.[7] ............................. C09F 7/06; C09F 7/08
(52) U.S. Cl. ........................ 252/182.18; 252/182.28; 252/183.11; 530/233; 554/31; 554/189
(58) Field of Search ................ 252/182.18, 182.28, 252/183.11; 530/233; 544/31, 190, 191, 192, 193; 554/31, 189, 190, 191, 192, 193

(56) References Cited

U.S. PATENT DOCUMENTS

| | | | |
|---|---|---|---|
| 2,343,644 A | | 3/1944 | Cawley |
| 2,411,111 A | * | 11/1946 | Ralston et al. ............... 554/31 |
| 2,421,157 A | | 5/1947 | Myers et al. |
| 2,450,235 A | | 9/1948 | Gee |
| 2,731,481 A | * | 1/1956 | Harrison et al. ............ 562/509 |
| 2,793,220 A | * | 5/1957 | Barrett et al. ............... 562/509 |
| 2,955,121 A | * | 10/1960 | Barrett et al. ............... 562/509 |
| 3,157,629 A | | 11/1964 | Patrick |
| 3,373,175 A | * | 3/1968 | Frankel ........................ 554/32 |
| 3,507,890 A | * | 4/1970 | Dieckelman et al. ....... 560/127 |
| 3,528,959 A | | 9/1970 | Patrick et al. |
| 3,753,968 A | | 8/1973 | Ward |
| 3,860,569 A | | 1/1975 | Ward |
| 3,923,768 A | | 12/1975 | Powers et al. |
| 3,943,118 A | | 3/1976 | Lehtinen |
| 3,980,630 A | | 9/1976 | Ishigami et al. |
| 4,052,425 A | | 10/1977 | Leonard |
| 4,156,095 A | | 5/1979 | Jevne et al. |
| 4,271,066 A | | 6/1981 | Matsuo et al. |
| 4,511,514 A | | 4/1985 | Cleary et al. |
| 4,659,513 A | | 4/1987 | Correia |
| 5,194,640 A | | 3/1993 | Cosgrove et al. |
| 5,442,081 A | * | 8/1995 | Behr et al. ..................... 554/26 |

OTHER PUBLICATIONS

Fremont, Lucie et al. "Preparation of oleic acid at 99.5% purity" *Ann.Biol.Biochim Biophys*, 1973, 13, 691–7 (abstract only).

Chernova et al. "Synthesis of oleic acid from fatty acids of tall oil" *Khim.Khim.Tekhnol.*, 1996,39,74–7 (abstract only).

Lakshminarayana et al. "A process for stearic acid and oleic acid from castor oil" *J.Oil Technol.Assoc.India*, 1990,22, 77–9 (abstract only).

Silverstone, G. Polymerization of Dehydrated Castor Acids Using an Acid Earth Catalyst, *Journal of the American Oil Chemists Society*, Aug. 1967, vol. 44 No. 8 pp 502–505.

* cited by examiner

*Primary Examiner*—Joseph D. Anthony
(74) *Attorney, Agent, or Firm*—Thomas W. Bornes, III

(57) ABSTRACT

A method whereby polyunsaturated components of fatty acids are conjugated and selectively polymerized in the presence of monounsaturated components, mainly oleic acid. Separation techniques are employed to isolate oleic acid and the linoleic acid-based dimer/trimer acids produced.

19 Claims, 1 Drawing Sheet

US 6,835,324 B1

METHOD FOR ISOLATING OLEIC ACID AND PRODUCING LINELOIC DIMER/TRIMER ACIDS VIA SELECTIVE REACTIVITY

RELATED APPLICATION

This application claims the benefit of U.S. Provisional Application No. 60/121,529 filed on Feb. 25, 1999, which is incorporated in it's entirety herein by reference.

FIELD OF THE INVENTION

This invention generally relates to a method for isolating oleic acid and producing lineloic dimer/trimer acids. More particularly, it concerns a process for reacting fatty acids which contain poly- and monounsaturates and then selectively polymerizing the polyunsaturates to produce the lineloic dimer/trimer acids.

BACKGROUND OF THE INVENTION

Oleic acid, a C-18 monounsaturated carboxylic acid, is widely used as the substrate for derivatives such as soaps, esters, amides, and polymers in applications such as surfactants, lubricants, corrosion inhibitors, and polyamide production. Use of oleic acid has an advantage over saturated acids in low temperature applications and has an advantage over mixtures with polyunsaturates owing to greater oxidative stability.

Oleic acid can be isolated from animal or vegetable sources via solvent extraction as taught in U.S. Pat. No. 2,421,157 to Myers et al.; U.S. Pat. No. 2,450,235 to Gee et al. and an article entitled "Preparation of oleic acid at 99.5% purity" by Fremont et al. (*Ann.Biol. Anim. Biochim, Biophys,* 1973, 13, 691–7). Oleic acid can also be separated from other fatty acids with the use of molecular sieves as disclosed in U.S. Pat. No. 4,511,514 to Cleary et al. As disclosed in articles entitled "Synthesis of oleic acid from fatty acids of tall oil" by Chernova et al., (*Khim.Khim.Tekhnol.,* 1996, 39, 74–7) and "A process for stearic acid and oleic acid from castor oil" by Lakshminarayana et al. (*J. Oil Technol. Assoc. India,* 1990, 22, 77–9), oleic acid can also be obtained from tallow or vegetable fatty acid sources by hydrogenation processes. These known processes involve multistage equipment and are typically very costly.

Other known methods have involved the use of catalyst systems to conjugate the olefins of polyunsaturated components within a fatty acid mixture providing a boiling point separation allowing an oleic acid-rich fraction to be distilled away from other components. Such methods are shown in U.S. Pat. No. 3,157,629 to Patrick; U.S. Pat. No. 3,923,768 to Powers et al.; and U.S. Pat. No. 4,271,066 to Matsuo et al. Other processes as described in U.S. Pat. No. 3,528,959 to Patrick et al.; U.S. Pat. Nos. 3,753,968 and 3,860,569 to Ward.; U.S. Pat. No. 3,980,630 to Ishigami et al.; and U.S. Pat. No. 4,659,513 to Correia, call for disproportionation of tall oil fatty acids at elevated temperature with various iodine catalyst systems. These processes require extended reaction times at elevated temperatures and large amounts of catalyst that causes isomerization of most of the oleic acid. Yields from these processes also suffer since undesired polymerization leaves dark-colored byproducts.

Another known method for isolating oleic acid from tall oil sources calls for forming an adduct of the conjugated diunsaturates in a Diels Alder protocol followed by distillation to separate a fraction rich in oleic acid. The use of stoichiometric amounts of dienophiles is required in this protocol to react with the diunsaturates which result in oleic acid as a byproduct and a C-21 diacid as the main product. U.S. Pat. No. 4,156,095 to Jevne et al.; U.S. Pat. No. 5,194,640 to Cosgrove et al. and in an article by McSweeney et al. *Tall Oil and Its Uses—II,* (Pulp Chemicals Association, NY, N.Y., 1987, p.33) are representative as disclosing such processes.

The present invention overcomes the disadvantages of the prior art processes by providing selective dimerization of linoleic acid in the presence of oleic acid from various fatty acid sources, preferably tall oil fatty acids. The process allows for the recovery of oleic acid from tall oil by first conjugating the diunsaturates followed by selective dimerization of these diunsaturates using either clay catalysis or t-butyl peroxide. Separation procedures such as distillation, then affords an oleic acid-rich fraction along with a C-36/C-54 co-product. By controlling reaction conditions, the diunsaturate content in the oleic acid obtained by this process can be very low, typically less than 10%, or between 10–15% depending on the desired application. The degree of isomerization of the oleic acid to elaidic acid and other isomers has also been minimized in the invention process. The C-36/C-54 co-product has characteristics of typical fatty acid dimer/trimers and can be used to produce polyamides/polyesters.

Thus, it is a general object of the invention to provide a process for isolating oleic acid and producing lineloic dimer/trimer acids by reacting fatty acids which contain poly- and monounsaturates and then selectively polymerizing the polyunsaturates.

Another object of the invention is to provide a process for obtaining a fatty acid from tall oil with oxidative stability and low temperature properties greater than tall oil.

It is another object of the invention to provide a process which can be modified to allow for isolation and separation of oleic acid fractions having different characteristics and properties.

A specific object of the invention is to provide a C-36/C-54 product which is useful in a number of applications including polyamide and polyester production.

Another specific object of the invention is that the yield of this process is quantitative less mechanical losses. No product is lost because the separation process involves no recyclables or heads/bottoms removal.

SUMMARY OF THE INVENTION

In the present invention, these purposes, as well as others which will be apparent, are achieved generally by providing a process for isolating oleic acid and producing linoleic acid-based dimer/trimer acids by first conjugating polyunsaturated components of fatty acids in the presence of monounsaturated components and then selectively polymerizing the polyunsaturated components to produce the dimer/trimer acids.

The fatty acid starting material includes monounsaturated components such as oleic acid, oleic acid isomers and non-conjugated linoleic acid. In general, the fatty acids used in the invention process are selected from tall oil fatty acids, vegetable fatty acids, animal fatty acids and marine fatty acids.

In the first process step, the fatty acids are treated with iodine and the mixture is heated to conjugate the polyunsaturated components. The amount of iodine in the conjugation reaction ranges from 0.01 to 0.15% by weight of the fatty acid. A co-catalyst may be further added to the mixture to enhance the conjugation of the polyunsaturates. Preferably the co-catalyst is selected from the group consisting of iron complexes, iron powder and bromine. In an alternate process embodiment, iron-iodine, $FeI_2$. itself can be used as the catalyst in amounts of approximately 0.2%. In any instance the mixture is heated to temperatures in the range of 200 to 260° C. for up to 6 hours to complete the conjugation reaction.

After the conjugation reaction, material is added to the mixture to cause polymerization of the conjugated polyunsaturated components and subject to further heat treatment and in some instances reacted under pressure. The catalytic material in this process step is preferably a clay catalyst but other materials such as t-butyl peroxide can be used. Additionally, lithium carbonate can be added to enhance the polymerization reaction. Typically, the clay catalyst is present in a range of from 1 to 4.7% by weight of the fatty acid. If t-butyl peroxide is used, it is present in stoichiometric amounts to the polyunsaturated components and if lithium carbonate is used is added in a range of 0.1 to 0.15% by weight of the fatty acid.

In the polymerization step, if a clay catalyst is used the mixture is preferably reacted under pressure up to 55 PSI at temperatures in the range of 170 to 190° C. for up to 6 hours. If t-butyl perxoide is used the mixture is further reacted at temperatures in the range of 120 to 135° C.

After polymerization the mixture is cooled to at least 130° C. If the polymerization process included the clay catalyst, phosphoric acid and/or diatomaceous earth elements are added to the cooled mixture and then filtered to remove the clay materials.

Finally, the oleic acid and lineloic dimer/trimer acids are separated from the reaction mixture using conventional separation techniques. Such separation techniques include a thin film evaporator or distillation columns. Generally, at least 50% oleic acid, typically over 60%, and preferably over 70%, is isolated by the invention process. The oleic acid isolated by this method has iodine values in the range of 80–100. Therefore, the oleic acid can be tailored depending on end use applications. Lower iodine values are preferred in applications where greater oxidative stability is required. Higher iodine values are preferred in applications where low temperature properties are desired.

Other objects, features and advantages of the present invention will be apparent when the detailed description of the preferred embodiments of the invention are considered with reference to the drawings, which should be construed in an illustrative and not limiting sense as follows: The fatty acid starting material includes monounsaturated components including oleic acid, oleic acid isomers and non-conjugated linoleic acid. In general, the fatty acid is selected from tall oil fatty acids, vegetable fatty acids, animal fatty acids and marine fatty acids.

DETAILED DESCRIPTION OF THE INVENTION

Figure 1:
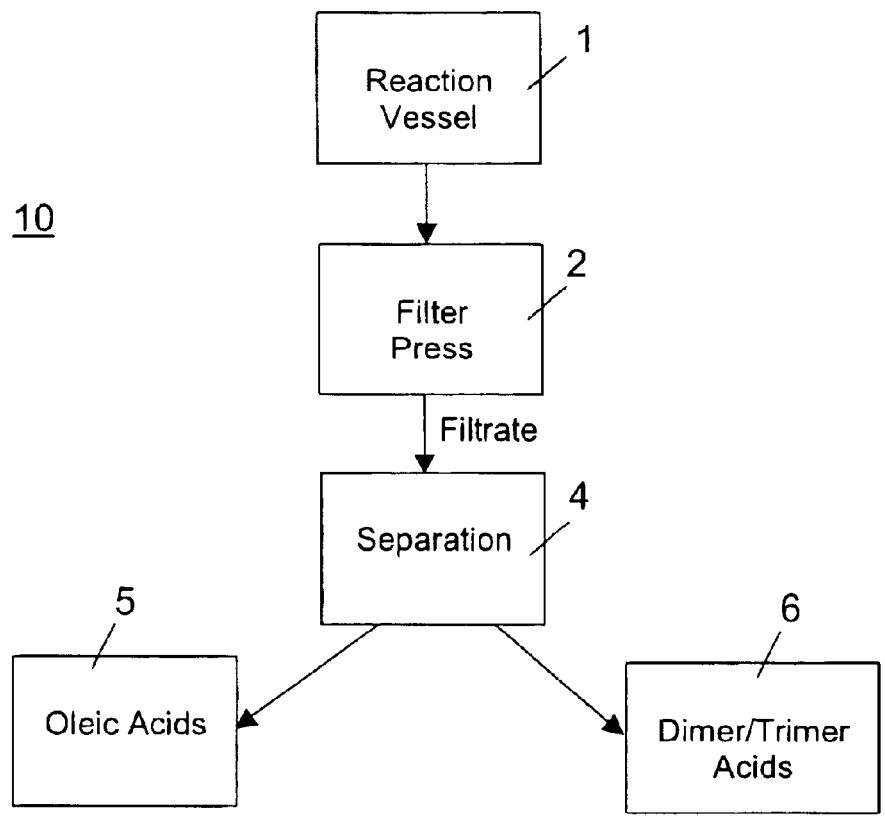
FIG. 1 is a schematic drawing of the process steps of the invention.

In accordance with the present invention a two-step process is provided for isolating oleic acid and producing linoleic acid based dimer/trimer acids. In general the process involves first conjugating polyunsaturated components of fatty acids in the presence of monounsaturated components and then selectively polymerizing the polyunsaturated components to produce the dimer/trimer acids.

As used throughout this specification the term polyunsatuated includes materials that are di- and triunsaturated. The fatty acids used in the invention process are selected from the group consisting of tall oil fatty acids, vegetable fatty acids, animal fatty acids and marine fatty acids. Typically the fatty acids include monounsaturated components such as oleic acid, oleic acid isomers and non-conjugated linoleic acid.

In the first process step, as illustrated in FIG. 1, the fatty acids are treated with iodine in the reaction vessel 1. The mixture is heated to conjugate the polyunsaturated components. The amount of iodine added to the reaction kettle ranges from 0.01 to 0.15% by weight of the fatty acid. A co-catalyst may be further added to the mixture to enhance the conjugation of the polyunsaturates. Preferably the co-catalyst is selected from the group consisting of iron complexes, iron powder and bromine. If the cocatalyst is iron(III)chloride, it is added in the range of 0.015 to 0.1% by weight of fatty acid. When the co-catalyst is iron powder, it is added in the range of 0.01 to 0.1% by weight of fatty acid. In an alternate process embodiment, iron-iodine, $FeI_2$, can be used as the catalyst, typically in an amount of 200 ppm.

In any instance the mixture in the reaction vessel 1 is heated to temperatures in the range of 200 to 260° C. for up to 6 hours to complete the conjugation reaction. The chemical reactions occuring in the Conjugation—Iodine treatment step and the resulting structures are illustrated in Reaction I below.

Reaction I - CONJUGATION

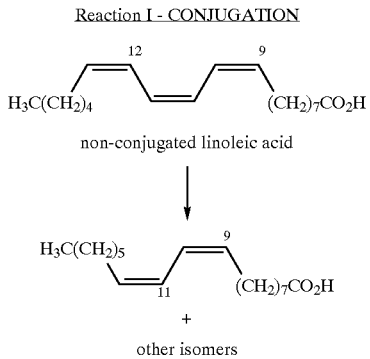

non-conjugated linoleic acid

+ other isomers

After the conjugation reaction, material is added to the mixture in the reaction vessel 1 and heated to temperatures in the range of 120 to 190° C. to cause polymerization of the conjugated polyunsaturated components. The catalytic material added in this process step is preferably a clay catalyst but other materials such as t-butyl peroxide can be used. Additionally lithium carbonate can be added to enhance the polymerization reaction. Typically, the clay catalyst is present in a range of from 1 to 4.7% by weight of the fatty acid. If t-butyl peroxide is used, it is present in stoichiometric amounts to the polyunsaturated components and if lithium carbonate is used is added in a range of 0.1 to 0.15% by weight of the fatty acid.

In the polymerization step, if a clay catalyst is used the mixture is preferably reacted under pressure up to 55 PSI at temperatures in the range of 170 to 190° C. for up to 6 hours. If the temperatures exceed 190° C. the oleic acid isomerizes, decreasing it's usefulness.

If t-butyl perxoide is used the mixture is further reacted at temperatures in the range of 120 to 135° C. for up to 8 hours.

The lithium carbonate is preferably used as an additive with the clay and enhances the polymerization of the conjugated and polyunsaturated components. Reaction II, below, illustrates the chemical reactions occuring in the Polymerization step and the resulting structures produced.

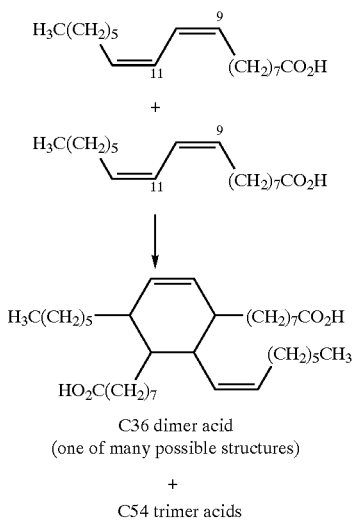

Reaction II-POLYMERIZATION

C36 dimer acid
(one of many possible structures)

+

C54 trimer acids

After polymerization the mixture is cooled to at least 130° C. If the polymerization process included the clay catalyst, phosphoric acid and/or diatomaceous earth elements are added to the cooled mixture and then filtered 2 to remove the clay materials. If no clay catalyst was used the mixture doesn't need to be filtered, making this step optional. The filtrate 3 liquid contains the reaction products which are then separated from the mixture using various techniques.

The oleic acid 5 and linoleic dimer/trimer acids 6 are separated from the filtrate using conventional separation techniques. Such separation techniques include a thin film evaporator or distillation columns 4. Typically, at least 50%, and preferably over 70% oleic acid is isolated by this process. The oleic acid formed by this process has an iodine value in the range of 80 to 103 dependent upon the process conditions.

The following examples illustrate various aspects of the invention but are not to be interpreted as limiting it. The tall oil fatty acids used in Examples 1 to 3 and 5 and 6 were Sylfat®FA-2 or Sylfat®95C both commercially available from Arizona Chemical Company, Panama City, Fla. These fatty acids typically contain 32% non-conjugated linoleic acids, 52% oleic acids, and 6% conjugated linoleic acids and have acid numbers in the range of 194–195. In all the examples, the reactions were done under nitrogen ($N_2$) atmosphere, unless specified otherwise. Yields are based on non-volatile components determined by microdistillation (0.15 mm Hg, 200° C., 45 min.)

As set forth in the examples below, certain physical properties, such as Gardner Color value and the Iodine values, of the dimer/trimer acids and oleic acid were measured. The test standards and procedures used in these examples for determining the Gardner Color value and Iodine value were as follows:

The Gardner Color value (American Society of Testing Materials standard practices "ASTM", ASTM D1544–80) is on a scale from 1 to 18, where 18 is dark and 1 is light. For example, 3– is slightly lighter than 3. As described in FATS AND OILS, second edition, by H. G. Kirschenbauer, copyright 1960, Reinhold Publishing Corp., Library of Congress Catalog Card No. 60-10506, Iodine number is a measure of unsaturation of the fat and is defined as the number of grams of iodine absorbed by 100 grams of the substance. Difficulty has been encountered in determination of unsaturation of oils that possess conjugated double bonds such as tung oil and terpene dimer. The Wijs method (described in ASTM D 1959–85) under certain conditions will give nonquantitive but reproducible results in the case of conjugated unsaturation.

The Iodine values as used herein are determined by procedure described in ASTM D 1959–85 which states that in the presence of conjugated double bonds Iodine values are empirical and are useful for comparative purposes but not as a measure of total unsaturation.

EXAMPLE 1

A tall oil fatty acid (1100 g), commercially available as Sylfat®FA-2 from Arizona Chemical, was added to a 2 L flask equipped with a stirrer. Iodine, $I_2$, (1.65 g), sulfur, $S_2$, (0.082 g) and Iron(III)chloride, $FeCl_3$, (0.16g) were added to the flask and the resulting mixture was heated to 235° C. and held at that temperature for 30 minutes. The mixture was cooled to 135° C. t-butyl peroxide (178 mL) was added and the resulting mixture stirred at 135° C. for 8 hours. This mixture was then cooled to 60–70° C. and high vacuum was employed to remove the t-butyl peroxide. The remaining composition was then distilled on a 2" Pope stainless steel, wiped film evaporator at 2.5 mm Hg and 245° C. to separate out the dimer/trimer acids and oleic acid components. Based on the weight of the starting material, approximately 38% dimer/trimer acids and 62% oleic acid was obtained. The properties of the oleic acid are listed in TABLE I below.

EXAMPLE 2

A tall oil fatty acid (480 g), commercially available as Sylfat®95C from Arizona Chemical, was added to a 2 L flask equipped with a stirrer. Iodine, $I_2$, (0.72 g), sulfur, $S_2$, (0.036 g) and Iron(III)chloride, $FeCl_3$, (0.070g) were added to the flask and the resulting mixture was heated to 235° C. and held at that temperature for 30 minutes. The mixture was cooled to ambient temperature and transferred to a 600 mL Parr autoclave. Clay (22 g, Dixie Bond Regular CB available from the Unimin Corporation) was added, as well as lithium carbonate, $Li_2CO_3$, (0.75 g) and water (3 g) and the resulting mixture heated to 190° C. and held at that temperature for 3 hours. Pressure was maintained at 55 PSI during this reaction.

After 3 hours at 190° C., the mixture was cooled to 130° C., the pressure was vented and phosphoric acid, $H_3PO_4$, (3 mL, 75% aq.) was added via piston-pump. The resulting mixture was held at 130° C. for 45 minutes and then a filter aid, FW-60 filter-aid (48 g, diatomaceous earth) was added to the mixture, which was then filtered.

The filtered composition was then distilled on a 2" Pope stainless steel, wiped film evaporator at 0.15 mm Hg and 200° C. to separate out the dimer/trimer acids and oleic acid components. Based on the weight of the starting material, approximately 33% dimer/trimer acids and 67% oleic acid was obtained. The properties of the oleic acid are listed in TABLE I below.

EXAMPLE 3

Reagent amounts and reaction conditions used in this example were identical to Example 2 except that the iodine, $I_2$, sulfur, $S_2$ and Iron(III)chloride, $FeCl_3$, treatment of the fatty acid was done at 200° C. for 1 hour.

The oleic acid was obtained in 70% yield and the dimer/trimer acids were obtained in 30% yield. Physical properties of the oleic acid are listed in TABLE I below.

EXAMPLE 4

The fatty acid material used in this example was a tall oil fatty acid commercially available as Sylfat®2F from Arizona Chemical. Sylfat®2F typically contains 30% oleic acid, 48% non-conjugated linoleic acid and 5% conjugated linoleic acids.

The fatty acid (500 g) was added to a 1 L flask. Iodine, $I_2$, (0.25 g) and Iron powder, Fe, (0.25 g) were added to the flask and the resulting mixture was heated to 235° C. for 3.5 hours and cooled to ambient temperature.

The mixture was then transferred to a 600 mL Parr autoclave. Clay (22 g), was added, as well as lithium carbonate, $Li_2CO_3$, (0.75 g) and water (3 g). The resulting mixture was heated at 180° C. for 3 hours while the pressure was maintained at 55 PSI.

The mixture was cooled and filtered using FW-60 filter-aid (10% by weight to the fatty acid).

The filtered composition was then distilled on a 2" Pope stainless steel, wiped film evaporator at 0.15 mm Hg and 200° C. to separate out the dimer/trimer and oleic acid components. Based on the weight of the starting material, approximately 46% dimer/trimer acids and 54% oleic acid was obtained. The properties of the oleic acid are listed in TABLE I below.

TABLE I

PHYSICAL CHARACTERISTICS OF OLEIC ACID

| PROPERTY | EXAMPLE 1 | EXAMPLE 2 | EXAMPLE 3 | EXAMPLE 4 |
|---|---|---|---|---|
| COLOR, GARDNER | 1+ | 2+ | 2+ | 5+ |
| ACID NO. | 193 | 192 | 192 | 191 |
| C18:1 | 76% | 78% | 76% | 67% |
| C18:2* | 12% | 4% | 14% | 9% |
| IODINE NO. | 87 | 80 | 103 | 100 |
| TITER, ° C. | 17 | 21 | 15 | 18 |

*Includes conjugated and non-conjugated C18:2

EXAMPLE 5

A tall oil fatty acid (273 kg), commercially available as Sylfat®FA-2 from Arizona Chemical, was added to a 100 gallon stainless steel reactor. Iodine, $I_2$, (68 g) and Iron powder, Fe, (68 g) were added to the reactor and the resulting mixture was heated to 245° C. and held at that temperature for 2.5 hours. The mixture was cooled to 60° C. Clay (8.1 kg, Dixie Bond Regular CB available from the Unimin Corporation) was added, as well as lithium carbonate, $Li_2CO_3$, (271 g) and water (1.8 kg) and the resulting mixture is heated to 180° C. and held at that temperature for 2.25 hours. Pressure was maintained at 55 PSI during this reaction.

The mixture was cooled and when the temperature reached 130° C., the pressure was vented and phosphoric acid, $H_3PO_4$, (1.6 kg, 75% aq.) was added. The resulting mixture was stirred at 130° C. for 80 minutes and filtered.

The dimer/trimer acids and oleic acid components were separated by wiped film distillation at 280° C. and 4 mm Hg vacuum. Based on the weight of the starting materials, yields were 32.5% dimer/trimer acids and 67.5% oleic acid. The properties of the oleic acid and dimer/trimer acids are listed in Table II below.

TABLE II

Oleic Acid and Dimer/Trimer acids isolated from conjugated tall oil by dimerization of polyunsaturates using clay catalyst

| PROPERTY | OLEIC ACID | DIMER/TRIMER ACIDS |
|---|---|---|
| Color, Gardner | 2− | 9+ |
| Acid No. | 193 | 189 |
| Iodine No. | 91 | 130 |
| Titer, ° C. | 19 | — |
| C18:1 | 78% | — |
| C18:2* | 9% | — |
| Dimer** | — | 78% |
| Polymer** | — | 22% |

*Includes conjugated and non-conjugated C18:2
**Determined by Gel Permeation Chromatography

EXAMPLE 6

A tall oil fatty acid, commercially available as Sylfat®FA-2 (240 g) from Arizona Chemical was added to a 1 L flask. Iron iodine, $FeI_2$, (0.060 g from Aldrich) was added to the flask and the resulting mixture was heated to 245° C. and held at that temperature for 4.0 hours. Gas chromatography analysis of the reaction mixture revealed that only 10% of the linoleic acid was non-conjugated.

EXAMPLE 7

The dimer/trimer mixture (436 g) from Example 5 was added to a 600 mL Parr autoclave. Clay (20.5 g, Dixie Bond Regular CB available from the Unimin Corporation) was added, as well as lithium carbonate, $Li_2CO_3$, (0.65 g) and water (1.5 mL) and the resulting mixture heated to 238° C. and held at that temperature for 2 hours. Pressure was maintained at 55 PSI during this reaction.

The mixture was then cooled and when the temperature reached 130° C., the pressure was vented and phosphoric acid, $H_3PO_4$, (1.0 mL, 75% aq.) was added. The resulting mixture was stirred at 130° C. for 45 minute. The mixture was cooled to 50° C. and FW-60 filter-aid (2.7 kg, diatomaceous earth) was added and the mixture was filtered. The final product characteristics are given in TABLE III below.

TABLE III

Dimer/Trimer acid after additional clay treatment

| PROPERTY | DIMER/TRIMER ACIDS |
|---|---|
| COLOR, GARDNER | 7 |
| ACID NO. | 194 |
| DIMER* | 74% |
| POLYMER* | 26% |

*Determined by Gel Permeation Chromatography

As shown in the examples, the two-step process of the invention, first conjugation and then polymerization provides advantage over prior art practice. The invention process provides conditions for dimerization that have been modified from known procedures to prevent isomerization and polymerization of the oleic acid that normally accompanies clay-catalyzed dimerization.

Known systems used to conjugate polyunsaturated components are typically very costly, unpractical on a commercial scale, yield several products, or cause significant isomerization of the monounsaturated components thereby detracting from their value and utility making them undesirable. The present invention process uses iodine, either alone or with a co-catalyst, in the conjugation reaction. To effect polymerization of the conjugated polyunsaturates a clay catalyst is used, with the reaction occuring, preferably under pressure. The oleic acid and linoleic dimer/trimer acids are separated using conventional separation techniques.

Advantageously, at least 50% of oleic acid, typically over 60%, and preferably over 70%, of oleic acid is achieved by this process. In addition, the oleic acid formed by this process has iodine values in the range of 80 to 103 depending on the process conditions.

Finally, variations of the invention process from the examples given herein are possible in view of the above disclosure. Therefore, although the invention has been described with reference to certain preferred embodiments, it will be appreciated that the processes may be modified, which are nevertheless within the scope and spirit of the invention as defined in the claims appended hereto.

What is claimed is:

1. A method for treating fatty acids comprising:
    adding an iodine catalyst selected from the group consisting of iodine ($I_2$) and iron iodine ($FeI_2$) to a fatty acid, which contains polyunsaturated components, to form a mixture; heating said mixture to cause conjugation of said polyunsaturated components;
    further reacting said mixture under heat with the addition of a polymerization catalyst to cause polymerization of the conjugated polyunsaturated components to produce a composition containing about 100% by weight of a mixture of linoleic dimer/trimer acids and oleic acid;
    and recovering, based on the weight of the starting material, at least 50% or more oleic acid from said composition.

2. The method according to claim 1, wherein said fatty acid includes monounsaturated components such as oleic acid, oleic acid isomers and non-conjugated linoleic acid.

3. The method according to claim 1, wherein said fatty acid is selected from the group consisting of tall oil fatty acids, vegetable fatty acids, animal fatty acids and marine fatty acids.

4. The method according to claim 1, wherein said iodine catalyst is added in amounts ranging from 0.01 to 0.15% by weight of the fatty acid.

5. The method according to claim 1, wherein a co-catalyst is further added to the mixture to enhance the conjugation of said polyunsaturates.

6. The method according to claim 5, wherein said co-catalyst is selected from the group consisting of iron complexes or iron powder.

7. The method according to claim 6, wherein the co-catalyst is iron (III) chloride added in the range of 0.015 to 0.1% by weight of the fatty acid.

8. The method according to claim 6, wherein the co-catalyst is iron powder added in the range of 0.01 to 0.1% by weight of the fatty acid.

9. The method according to claim 1, wherein said mixture is first heated to temperatures in the range of 200 to 260° C. for up to 6 hours.

10. The method according to claim 1, wherein said polymerization catalyst added to cause polymerization is a clay catalyst present in an amount of 1 to 4.7% by weight of the fatty acid.

11. The method according to claim 10, wherein said mixture is reacted under pressure up to 55 PSI and at temperatures in the range of 170 to 190° C. for up to 6 hours.

12. The method according to claim 1, wherein said polymerization catalyst added to cause polymerization is t-butyl peroxide present in stoichiometric amounts to said polyunsaturated components.

13. The method according to claim 12, wherein said mixture is reacted at temperatures in the range of 120 to 135° C. for up to 8 hours.

14. The method according to claim 1, wherein a further catalyst is added to said material to enhance polymerization of said conjugated polyunsaturated components.

15. The method according to claim 1, wherein said further catalyst is lithium carbonate added in amounts between 0.1 to 0.15% by weight of the fatty acid.

16. The method according to claim 1, wherein after said polymerization, said mixture is cooled to at least 130° C.

17. The method according to claim 1, wherein phosphoric acid and diatomaceous earth elements are added to said cooled mixture and is then filtered.

18. The method according to claim 1, wherein said oleic acid and linoleic dimer/trimer acids are separated from said composition using conventional separation techniques.

19. The method according to claim 18, wherein said separation techniques included thin film evaporator or distillation columns.

* * * * *